United States Patent [19]

Johansson

[11] Patent Number: 4,783,448
[45] Date of Patent: Nov. 8, 1988

[54] METHOD FOR CLEANSING AN INFECTED SORE

[75] Inventor: Olof J. A. Johansson, Olofström, Sweden

[73] Assignee: Perstorp AB, Perstorp, Sweden

[21] Appl. No.: 501,780

[22] Filed: Jun. 7, 1983

[51] Int. Cl.4 ............................................. A61K 31/70
[52] U.S. Cl. ...................................... 514/57; 514/54; 514/59; 514/60
[58] Field of Search ....................... 424/180; 536/112; 514/59, 60, 57

[56] References Cited

U.S. PATENT DOCUMENTS 2,811,517 9/1957 Novak .................................. 536/112
4,002,173 1/1977 Manning et al. ..................... 536/112
4,010,259 3/1977 Johansson ............................ 424/180

Primary Examiner—Johnnie R. Brown
Assistant Examiner—Elli Peselev
Attorney, Agent, or Firm—Stevens, Davis, Miller & Mosher

[57] ABSTRACT

The present invention relates to a method for cleansing a fluid-discharging infected sore located on the exterior of the body by avoiding the formation of an escar on the sore.

13 Claims, No Drawings

METHOD FOR CLEANSING AN INFECTED SORE

The present invention relates to a method for cleansing an infected sore located on the exterior of the body.

Healing of sores on the exterior of the body is a very old medical problem. To achieve an effective healing of such a sore it is necessary to keep it clean from dirt, bacteria etc. It is also important not to damage the sensitive epithelia cells in connection with necessary changes of bandages, dressings etc.

Due to the inclination of the sore excudate to coagulate a scab is quickly formed, whereby the bandage for example might stick to the sore. This rapid formation of a scab results in a number of disadvantages. The scab is preventing a continuous cleansing of the sore resulting in a delayed healing.

Moreover, the necessary change of air is prevented which favour the growth of anaerobic bacteria.

At the normal treatment of sores the epithelia cells formed at the healing process are damaged at the change of bandages etc. Such treatment is of course very painful to the patients. The problems are especially evident at serious sores, such as leg ulcers, decubitus ulcers, burn sores and lepra sores, for instance.

An effort has been made before to influence the coagulation process and the resulting scab formation on an infected sore by applying to the sore a layer of absorbent polymer particles having specific gel chromatographic properties as shown in the U.S. Pat. No. 4,225,580. It is stated in said patent that the formation of the scab is influenced by a gel chromatographic separation of specific compounds of the sore excudate, which are essential for the coagulation process, especially fibrinogen and calcium chloride. It is pointed out in said patent that the high molecular weight fibrinogen migrates upwards towards the outer boundaries of the mass of polymer particles applied to the sore at a progressively increasing concentration. At the same time the low molecular weight compounds necessary for the coagulation process pass at a slower rate through the mass of polymer particles. In this way a gel chromatographic separation, i.e. selective absorption is achieved.

It is stressed in said patent that a scab is formed on the sore, however, spaced a bit from the sore surface.

As mentioned in the above patent the polymer is selected so that particles of the polymer in a water-swollen state could be used in a column for conventional gel filtration of fibrinogen from low molecular weight compounds of the sore excudate.

The above problems in connection with the formation of a scab on a sore have not been solved by the method of the U.S. Pat. No. 4,225,580. Thus, the manufacturer of DEBRISAN ®, the commercial product covered by the U.S. patent has himself indicated in the Swedish medical periodical, Läkartidningen No. 37, (1980), pages 3078 and 3079, that DEBRISAN ® is difficult to apply and to remove.

The reason why DEBRISAN is difficult to remove is that a scab is formed on the sore.

According to the present invention a method for cleansing an infected sore by means of a new unique principle has been brought about.

Thus, one embodiment of the invention relates to a method for cleansing a fluid-discharging infected sore located on the exterior of the body by avoiding the formation of an escar on the sore. The method comprises applying to the sore a particulate mass of dry water-absorbing, water-insoluble but swellable polymer particles comprising polymeric or polymerized carbohydrates or sugar alcohols cross-linked into a three-dimensional network held together by bonds of covalent nature wherein the polymer contains anionic groups in acid form and/or iodine combined with the polymer. One gram of the polymer swells in the presence of water to absorb at least one gram of water.

Said particulate mass is maintained in contact with said sore for a sufficient length of time to permit fluid discharged from the sore to be absorbed by the polymer particles. The escar formation is avoided by preventing the normal coagulation process by means of the action of the anionic groups in acid form and/or the iodine on said fluid discharged from the sore. The particulate mass and materials absorbed from the sore are subsequently removed.

Another embodiment of the invention relates to a method for cleansing an infected open sore located on the exterior of the body by preventing the formation of a scab on the sore. The method comprises applying to the sore an effective amount of a particulate mass of dry water-insoluble absorbent and absorbable iodophor particles containing 0.01–35% by weight of iodine and having an average particle size of 10–1000$\mu$ and comprising a starch or a dextrin polymer cross-linked into a three-dimensional network held together by bonds of covalent nature and with iodine complexed to the polymer. One gram of the iodophor swells in the presence of water to absorb 1–30 grams of water. Said particulate mass is maintained in contact with said sore for a sufficient length of time to permit such fluid to be absorbed by the particles and iodine in the iodophor to be released to the sore.

Thereafter the resulting particulate mass is removed from contact with the sore, whereby, by virtue of a rapid chemical reaction with iodine released from the iodophor the chemical structure of fibrinogen in said fluid is modified already at the surface of the sore and thus the normal coagulation process is prevented and an escar formation is avoided on the sore and bacteria are killed by the iodine and may later on be readily removed together with the polymer particles, the chemically modified fibrinogen and other components discharged from the infected sore.

Thus, according to the present invention the normal coagulation process and scab formation are generally prevented by means of an action of the anionic groups in acid form of the polymer and/or the iodine on the fibrinogen in the fluid discharged from the sore.

If the polymer as according to one embodiment of the invention contains iodine, the iodine will cause a change of the chemical structure of the fibrinogen resulting in a change also of the physical-chemical properties of the fibrinogen. This change of the physical-chemical properties is shown by a precipitation of the fibrinogen at the contact with the iodine.

According to another embodiment of the invention the polymer contains anionic groups in acid form. Then said groups are causing a decrease of the pH of the fluid discharged from the sore.

Accordingly, by an ion exchange process hydrogen ions are liberated preferably by sodium and calcium ions in said fluid.

At the decrease of the pH the physical-chemical properties of the fibrinogen are changed in such a way that the fibrinogen loses its coagulation properties.

According to another very advantageous embodiment of the invention the polymer contains anionic groups in acid form and is combined with iodine. Then an unexpectedly strong inactivation of the coagulation properties of the fibrinogen is obtained.

The anionic groups can contain sulphonic acid groups, carboxylic acid groups or phosphoric acid groups in acid form.

The polymer particles used according to the invention are selected so that they prevent in a liquid-swollen state the normal coagulation process by a rapid inactivation of the coagulation properties of the fibrinogen by means of the action of anionic groups in acid form and/or iodine on the fluid discharged from the sore. This also means that the fibrinogen is not migrating in the normal way according to gel chromatographic principles. Therefore, in a column for conventional gel filtration purposes the fibrinogen cannot be separated by gel filtration techniques.

The polymer particles used according to the invention are either previously known or can be prepared according to known methods such as those described in the U.S. Pat. Nos. 3,275,576 and 4,010,259.

The polymer particles are dry, water-absorbing but water-insoluble. The particles are swelling in a water containing liquid to form a gel. The polymer particles comprise polymeric or polymerized carbohydrates or sugar alcohols cross-linked into a threedimensional network held together by bonds of a covalent nature. The carbohydrates polymers can be natural occuring polysaccharides such as cellulose, starch, inulin or degradation products thereof such as dextrin or reduction products such as sugar alcohols.

The carbohydrates can be low molecular weight products such as oligo-, di- and monosaccharides or reduction products thereof such as saccharose, maltose, glucose, fructose, sorbitol, mannitol etc. which are polymerized.

Furthermore, the carbohydrates can be synthetic polymers such as dextrans or levans or reduction or degradation products thereof, such as sugar alcohols.

The carbohydrates can be derivatives of the abovementioned products, for example containing anionic, cationic, or nonionic groups. Hydroxyethylstarch, hydroxypropylstarch, carboxymethylstarch, sulphopropylstarch, sulphoethylstarch, diethylaminoethylstarch, β-morfolinoethylstarch, starchphosphates and the corresponding dextrin, cellulose and dextran derivatives constitute examples of suitable carbohydrate derivatives.

In accordance with the invention the carbohydrate polymer is a hydroxyl group-containing three-dimensional network held together by bonds of a covalent nature and built up by hydroxyl group-containing polymer molecules cross-linked by means of bridges connected to said polymer molecules by ether bonds. The bridges may be straight or branched aliphatic saturated hydrocarbon chains substituted by one or more hydroxyl groups and containing 3-20 carbon atoms, preferably 3-10 carbon atoms, said chains being optionally broken by one or more oxygen atoms. The polymeric product is insoluble but swellable in water to form a gel, said gel in a fully water-swollen state containing more than 30%, preferably more than 50% and most preferably more than 60% by weight of water and less than 97%, preferably less than 95% and most preferably less than 90% by weight of water.

In accordance with the invention the carbohydrate polymers are cross-linked in alkaline aqueous solution by means of at least bifunctional bridge forming substances of the type

and

wherein x, y and z are each a halogen atom, preferably chloro or bromo, and $a_1$ and $a_2$ are each a straight or branched aliphatic, saturated hydrocarbon chain having one or more hydroxyl groups and preferably containing 3-20 carbon atoms, e.g. 3-10 carbon atoms, said chain being optionally broken by one or more oxygen atoms or corresponding epoxide compounds obtainable by splitting-off hydrogen halide from the compound (I) or (II). As examples of bifunctional substances of the formula $x-a_1-z$ and corresponding epoxide compounds capable of being obtained from $x-a_1-z$ by splitting off hydrogen halides can be mentioned:

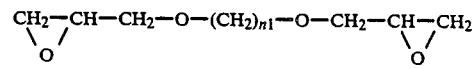

wherein nl is an integer from 2 to 4 and

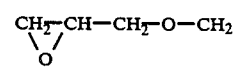

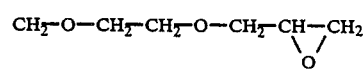

and

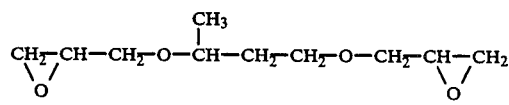

and

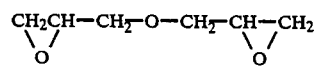

and

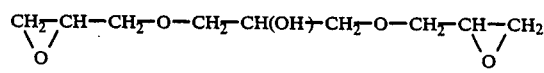

or corresponding halogen hydrins and bifunctional glycerol derivatives of the formula $X-CH_2-CH(OH)-CH_2-Z$ e.g. dichlorohydrin and dibromohydrin or corresponding epoxide compounds of the formula

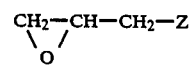

such as epichlorohydrin and epibromohydrin, obtainable by splitting off hydrogen halides. Another example of such a bifunctional compound is 1.2-3.4-diepoxybutane of the formula

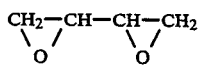

As example of trifunctional bridge forming epoxide compounds corresponding to compounds of the formula

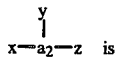 is

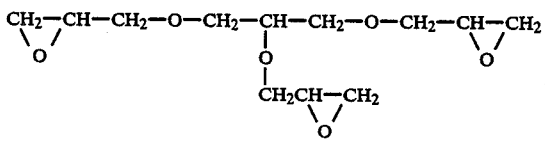

The polymer which is usually water-soluble is reacted with a sufficient quantity of a substance which is at least bifunctional to form a water-insoluble gel i.e. a practically infinite three-dimensional network. Thus, the aforementioned hydroxyl group-containing carbohydrates are usually reacted in alkaline aqueous solution with one of the aforementioned bridge forming substances in a quantity such that a gel which is insoluble in water but capable of undergoing swelling therein is formed by cross-linking of the polymer chains. Diepoxides and corresponding halohydrins react, for example, with hydroxyl groups to form ether bonds.

The absorption ability (swelling capacity) of the polymer particles is in this description defined as the gel bed volume (in ml) obtained when 1 g of dry polymer particles is completely swelled in the swelling agent.

In accordance with the invention the hydrophilic property of the polymer is such that 1 g of the dry polymer particles swelled in the presence of water absorbs at least 1 g of water but less than 100 g. For example, the polymer particles may absorb 1–50 g of water, 2–30 g, 2–15 g or 2–10 g depending on the type of sore to be cleansed.

In accordance with the invention, the dry polymer particles may have an average particle size within the range of 10–1000μ, preferably 20–500μ.

Usually, the average particle size is 30–400μ, preferably 50–300μ. Generally, the average particle size should be small when the polymer particles are applied in the form of an ointment.

The polymer particles used may be spherical (e.g. obtained by so-called bead polymerization processes) or have irregular shape (e.g. obtained by so-called bulk polymerization and grinding).

If the polymer used according to the present invention is selected from starch, dextrin or derivatives thereof, such as hydroxyethyl starch, carboxymethyl starch and the corresponding dextrin derivatives, the polymer is absorbable by body fluids. That means that the polymer particles are slowly broken down enzymatically to water-soluble fragments by the influence of α-amylase in the aqueous body fluid. In some cases the use of such polymers is advantageous, since the polymer particles will gradually disappear as water-soluble fragments if all of the particles should not have been removed after the cleansing process.

When the polymer particles according to the invention are combined with iodine, the iodine can be complexed to the polymer particles to an iodophor. Then the iodine can be slowly released at contact with the fluid discharged from the sore. Moreover, the iodine can be absorbed or adsorbed to the polymer particles.

The iodine content of the polymer particles may be varied within wide limits depending on the possible presence of anionic groups in acid form in the polymer particles. Generally, the iodine content is 0.01–35 percent by weight, preferably 0.1–10 percent by weight. Usually, the iodine content is only 0.1–5, most preferably 0.4–2 percent by weight, especially if anionic groups in acid form are present in the polymer particles.

When the polymer particles contain anionic groups in acid form the ion exchange capacity of said groups may amount to 0.1–5 meq/g. If the polymer particles in addition to said anionic groups in acid form are combined with iodine the ion exchange capacity may be in the lower part of the above range, for example 0.1–2 meq/g.

The ion exchange capacity should also be regulated with regard to the amount of fluid discharged from the sore. Consequently, the ion exchange capacity should be rather high if the sore to be treated is highly discharging.

In accordance with the invention the polymer particles may be applied as such to the sore or mixed with inert fillers, such as cellulose powder and cotton fibres. The polymer particles together with optional fillers may also be used in the form of an ointment, a bandage, a plaster or other dressings.

According to the invention, the dry polymer particles may be applied in the form of a layer on the sore in a manner to enable the aqueous fluid on said surface to be absorbed by the polymer, whereafter the layer of particles with absorbed material therein is removed from the sore. The process can be repeated one or more times until the desired degree of cleaning is obtained. If the cleansing process is repeated this may be done at an interval of 8, 12 or 24 hours for instance depending on the kind of the sore.

The material absorbed by the polymer particles comprises dirt, bacteria, nasty-smelling products etc.

According to the invention the scab formation is effectively avoided resulting in an extraordinarily good cleansing effect. Moreover, the polymer particles together with absorbed material can easily be removed. Therefore, the epithelia cells formed at the healing process are not damaged and the treatment is not painful to the patients.

The invention will be further explained in connection with the embodiment examples below, of which Examples 1–4 relate to the manufacture of the polymer particles used according to the present invention. The polymer particles of Example 1 do not contain any anionic groups, but are combined with iodine, while the polymer particles of Example 2 contain anionic groups in acid form and are combined with iodine to an iodophor.

The polymer particles of Examples 3 and 4 contain anionic groups in acid form, but are not combined with iodine.

Examples 5, 6, 7, 9 and 10 illustrate the method of the present invention, while Example 8 illustrates the manufacture of an ointment used according to one embodiment of the invention.

Examples 11 and 12 illustrate gel chromatographic tests with polymers used according to the present invention, while Example 13 relates to a comparative gel chromatographic test with polymer particles not having the properties necessary according to the present invention, since they did not contain anionic groups in acid form and were not combined with iodine.

EXAMPLE 1

750 g of commercially available spherical dextran polymer particles (Debrisan®, Pharmacia, Sweden) were swelled to a gel in 5750 ml of water, while stirring. A solution of 62.5 g of iodine in 500 ml of ethanol was added to the swelled gel.

The mixture was stirred for 2 h at 35° C. The iodophor gel obtained was filtered off and washed with 600 ml of water. Then the gel was dried at room temperature for 15 h and subsequently at 70° C. for 8 h.

Yield: 755 g. Analysis; 2.35% iodine and 4.2% moisture; swelling capacity 3.8 ml/g; average particle size 200μ.

EXAMPLE 2

100 g carboxymethyl substituted dextrin polymer particles cross-linked with epichlorohydrin were produced according to U.S. Pat. No. 3,275,576. The anionic carboxymethyl groups were present in salt form. The anionic carboxymethyl groups were then transformed from salt form to acid form according to conventional methods. The polymer was combined with iodine according to U.S. Pat. No. 4,010,259 and had the following properties:

Swelling capacity 7.7 ml/g; average particle size 215μ; ion exchange capacity 0.40 meq/g; iodine content 0.9% and moisture content 4.3%.

EXAMPLE 3

A sulphopropyl substituted hydroxyethyl cellulose cross-linked with 1,2-3,4 diepoxy butane and produced according to U.S. Pat. No. 3,275,576 had the following properties:

Swelling capacity 11.7 ml/g; average particle size 60μ; ion exchange capacity 3.1 meq/g and moisture content 5.1%.

EXAMPLE 4

100 g carboxymethyl substituted dextrin polymer particles cross-linked with epichlorohydrin were produced according to U.S. Pat. No. 3,275,576. The anionic carboxymethyl groups were present in salt form. The anionic carboxymethyl groups were then transformed from salt form to acid form according to conventional methods. The polymer particles had the following properties:

4.5% moisture; swelling capacity 7.9 ml/g; average particle size 210μ; ion exchange capacity 0.42 meq/g.

EXAMPLE 5

A 56 year old man had suffered for 25 years from a 35 square cm large leg ulcer located on the lower part of his right leg. The ulcer was infected, extremely painful and discharged a nasty-smelling fluid. Previous attempts to cleanse and heal the ulcer had been in vain. Bacteriological tests showed a pronounced growth of *S. aureus* and *P. aeruginosa*. For the purpose of cleansing and healing the ulcer it was washed with physiological saline solution. Thereafter a 4 mm thick layer of the iodine containing polymer particles according to Example 2 was applied directly to the ulcer by a castor. The ulcer was covered with a sterile gauze bandage. The cleansing treatment was repeated at an interval of 24 hours according to the same procedure as mentioned above.

Before the application of a new layer of polymer particles to the ulcer, previously applied particles with absorbed excudate, bacteria etc. were washed away from the ulcer with physiological saline solution. This could easily be done, since no scab had been formed on the ulcer.

After a treatment of 2 days the ulcer was clinically clean and no signs of infection could be observed. The ulcer was completely healed after a treatment of 18 days.

EXAMPLE 6

A woman, 81 years of age had suffered for 6 months from a sore 3 cm in diameter located on the left leg close to the anklebone. The sore was infected with different bacterial species and it discharged fluid. Previous attempts to cleanse and heal the sore had not given any positive result. For the purpose of cleansing and healing the sore it was treated according to Example 5 with the dry spherical iodine containing dry polymer particles produced according to Example 1. The particle layer applied to the sore had a thickness of about 3 mm.

After 3 days the sore was found to be clinically clean with healthy granulation and no sign of infection. The sore was healed completely after a treatment of 8 days.

EXAMPLE 7

A 6 year old girl had scalded her right foot with boiling coffee over an area corresponding to about double the size of her palm. After six days an infection of the sore had developed in spite of repeated and careful hygiene. The sore could be characterized as a pronounced discharging one.

For the purpose of cleansing the sore, there was applied directly thereto a 4 mm thick layer of dry water-insoluble polymer particles obtained according to Example 3. The treatment was carried out according to the method described in Example 5, but at an interval of 8 hours. The sore was healed without complications in 6 days and from the second day and further on the girl suffered no pain during the treatment process or when the polymer particle layer had to be changed.

EXAMPLE 8

An ointment was prepared in the following way. Dry polymer particles were produced according to Example 2. However, the polymer particles had an average particle size of 50μ. 100 g of the dry iodine containing polymer particles were thoroughly mixed with 60 g polyethyleneglycol (Macrogolum® 400, Apoteksbolaget, Sweden) and 40 g polyethyleneglycol (Macrogolum® 300 et 1540 AKL, Apoteksbolaget, Sweden).

EXAMPLE 9

A 41 year old man suffered from a skin inflammation on his chest. The inflammation was caused by a virus (Herpes Zoster). The inflammation was itching and fluid discharging. The inflamed skin area was coated with a layer of the ointment prepared according to Example 8 and the ointment layer was covered with a sterile gauze bandage. The layer of ointment and bandage was changed at an interval of 12 hours.

The ointment layer together with absorbed excudate was washed away with physiological saline solution. This local skin treatment was combined with systemic antibiotic treatment. After a treatment for 5 days the inflammation had been healed and the itching had completely disappeared.

EXAMPLE 10

A man, 62 years of age, totally lame from the stomach and downwards and suffering from multiple schlerosis had developed a pressure sore from anterior superior iliac spine and downwards as a result of his staying to bed. Previous attempts to cleanse and heal the six month old sore had been in vain. The sore was infected and discharging pus and debris. For the purpose of cleansing and healing the sore was filled with polymer particles produced according to Example 2. The sore was covered with a sterile gauze bandage. The cleansing treatment was repeated at an interval of 12 hours. Before the application of a new layer of polymer particles to the sore, earlier applied polymer particles together with absorbed excudate were washed away from the sore with physiological saline solution. After 3 days of treatment of the sore the patient suffered no pain during treatment or when the polymer particle layer was changed. The sore was clinically clean and healthy granulation appeared. The sore was healed completely after 14 days of treatment.

EXAMPLE 11

Iodine containing polymer particles produced according to Example 2 were swelled in distilled water and packed in a column for conventional gel filtration purposes. A Pharmacia gel column SR 25/45 was used. 1 ml of a fibrinogen in physiological saline solution containing 0.5% weight/volume of fibrinogen was added to the top of the column followed by an elusion solution consisting of physiological saline solution. The eluent was collected in 10 ml test tubes using a fraction collector, each fraction contained 6 ml of eluent. 240 ml of eluent was added to the column giving 40 test tubes of 6 ml each. The contents of different test tubes were analyzed for fibrinogen by using a UV-spectrophotometer type Unican SP 800. To avoid an interference of the detection and analysis of the fibrinogen by influence of elemental iodine released from the polymer 2 drops of 0.1N sodiumthiosulphate solution was added to the fractions of the different test tubes to reduce the elemental iodine to iodide. The eluent amounting to 240 ml represented approx. 1.5 times the total volume of the packed swelled polymer particles. No fibrinogen could be found in any fraction. If normal gel chromatographic separation had occured the fibrinogen should have appeared before fraction No. 20. Thus, no migration of fibrinogen through the column was obtained. Further investigations verified that the fibrinogen had been precipitated by the iodine in the polymer particles.

EXAMPLE 12

The gel chromatographic test according to Example 11 was repeated. However, now the polymer particles obtained according to Example 4 were used instead. No fibrinogen could be detected in the 40 fractions collected. Thus, no migration and gel chromatographic separation of fibrinogen in the column was obtained.

EXAMPLE 13

The gel chromatographic test according to Example 11 was repeated. However, now the commercial cross-linked dextran polymer DEBRISAN® (Pharmacia AB, Sweden) was used instead. This product does not contain iodine or anionic groups in acid form. In this case a normal gel chromatographic separation and migration of the fibrinogen in the column was obtained.

The present invention is not limited to the embodiments shown, since these can be modified in different ways within the scope of the present invention.

I claim:

1. A method for cleansing a fluid-discharging infected sore located on the exterior of the body by avoiding the formation of an escar on the sore, which method comprises applying to the sore an iodine-free particulate mass of dry water-absorbing, water-insoluble but swellable polymer particles consisting essentially of dextran, starch, cellulose, or derivatives thereof, cross-linked into a three-dimensional network by means of bridges connected to the molecules of said polymer by ether bonds, wherein the polymer contains anionic groups selected from sulphonic acid groups, carboxylic acid groups, and phosphoric acid groups in acid form, one gram of which polymer swells in the presence of water to absorb at least one gram of water, maintaining said particulate mass in contact with said sore for a sufficient length of time to permit fluid discharged from the sore to be absorbed by the polymer particles and avoiding the escar formation by precipitation of the fibrinogen at the surface of the sore and thus preventing the normal coagulation process by means of the action of said anionic groups in acid form on the fibrinogen in said fluid discharged from the sore, and removing the particulate mass and materials absorbed from the sore.

2. A method according to claim 1, wherein the polymer is cross-linked by means of bridges comprising straight or branched aliphatic saturated hydrocarbon chains bound to said polymer molecules by ether linkages, said hydrocarbon chains containing 3–20 carbon atoms and being substituted by one or more hydroxyl groups.

3. A method according to claim 2, wherein the hydrocarbon chains are interrupted by one to three oxygen atoms.

4. A method according to claim 1, wherein the polymer is cross-linked with epichlorohydrin.

5. A method according to claim 1, wherein the polymer particles have an average particle size of 10–1000$\mu$.

6. A method according to claim 1, wherein the polymer particles have an average particle size of 20–500$\mu$.

7. A method according to claim 1, wherein one gram of the polymer absorbs 2–15 g of water.

8. A method according to claim 1, wherein one gram of the polymer absorbs 2–10 g of water.

9. A method according to claim 1, wherein the polymer is applied to the sore to be cleansed in the form of a layer so that the material discharging from the sore is absorbed by the polymer, the polymer layer together with absorbed material therein being removed from the sore and the treatment repeated until the desired degree of cleanliness has been obtained.

10. A method according to claim 1, wherein the polymer is absorbable by body fluids, and is selected from starch, dextrin and derivatives thereof containing sulphonic acid groups, carboxylic acid groups or phosphoric acid groups in acid form.

11. A method according to claim 1, wherein the ion exchange capacity of the anionic groups in acid form of the polymer is 0.1–5 meq/g.

12. A method according to claim 1, wherein the normal coagulation process is prevented by the anionic groups in acid form, which cause a decrease of the pH of the fluid discharged from the sore and thereby a precipitation of the fibrinogen in said fluid.

13. A method according to claims 1 or 2, wherein the polymer particles are applied to the sore in the form of an ointment, a dressing, or a bandage.

* * * * *